US012568942B2

(12) United States Patent
Unger

(10) Patent No.: US 12,568,942 B2
(45) Date of Patent: Mar. 10, 2026

(54) INSECT FARMING WITH PRE-DOSED UNITS

(71) Applicant: Livin Farms AgriFood GmbH, Vienna (AT)

(72) Inventor: Katharina Unger, Vienna (AT)

(73) Assignee: Livin Farms AgriFood GmbH, Vienna (AT)

( * ) Notice: Subject to any disclaimer, the term of this patent is extended or adjusted under 35 U.S.C. 154(b) by 0 days.

(21) Appl. No.: 18/883,202

(22) Filed: Sep. 12, 2024

(65) Prior Publication Data

US 2025/0081947 A1 Mar. 13, 2025

(30) Foreign Application Priority Data

Sep. 13, 2023 (EP) ..................................... 23197144

(51) Int. Cl.
*A01K 67/30* (2025.01)
(52) U.S. Cl.
CPC ........ *A01K 67/30* (2025.01); *A01K 2227/706* (2013.01)
(58) Field of Classification Search
CPC .......................... A01K 67/30; A01K 2227/706
See application file for complete search history.

(56) References Cited

U.S. PATENT DOCUMENTS 10,448,623 B1 * 10/2019 Selby ..................... A01K 67/30
11,291,190 B1 * 4/2022 Peeters ................ A01K 29/005

11,490,604 B2 * 11/2022 Massaro ................ A01K 67/30
11,570,972 B2 * 2/2023 Comparat .............. A01K 67/30
11,723,349 B2 * 8/2023 Lepek ................. G06F 18/2431
119/6.5
11,730,152 B1 * 8/2023 Freeman .............. B07C 5/3427
382/110
11,950,579 B2 * 4/2024 Lepek ................... A01M 1/223
2003/0188698 A1 * 10/2003 Donaldson ............. A01K 67/30
119/678

(Continued)

FOREIGN PATENT DOCUMENTS

CN 115968837 4/2023
TW M609282 3/2021

(Continued)

OTHER PUBLICATIONS

Europe Search Report/Office Action (EP SR/OA) conducted in counterpart Europe Appln. No. 23197144.1 (Mar. 7, 2024).

*Primary Examiner* — Monica L Perry
*Assistant Examiner* — Aaron M Rodziwicz
(74) *Attorney, Agent, or Firm* — GREENBLUM & BERNSTEIN, P.L.C.

(57) ABSTRACT

A dosing device, arrangement and method for insect farming. The dosing device includes a storage unit designed to store a package containing a predetermined quantity of insects; a package containing insects stored in the storage unit; and a robot, which is arranged in a region of the at least one storage unit and at least one container, which is provided with a container substrate, is configured to remove the package containing the insects from the storage unit and to move the package with the insects to the container. The robot unit is further configured to directly or indirectly deposit the insects from the package into the container substrate.

20 Claims, 2 Drawing Sheets

(56)  References Cited

U.S. PATENT DOCUMENTS

| | | | | |
|---|---|---|---|---|
| 2016/0066552 A1* | 3/2016 | Arsiwalla | .............. | A01K 67/33 |
| | | | | 119/6.5 |
| 2018/0070566 A1* | 3/2018 | Comparat | .............. | A01K 67/30 |
| 2022/0217957 A1* | 7/2022 | Baptistan | .............. | A01K 67/30 |
| 2023/0363363 A1* | 11/2023 | Lepek | .................... | A01K 67/30 |
| 2024/0008448 A1* | 1/2024 | Gelder | .................. | G01G 17/08 |
| 2024/0032518 A1* | 2/2024 | Slade | .................... | A01K 67/30 |

FOREIGN PATENT DOCUMENTS

| | | |
|---|---|---|
| WO | 2021/148894 | 7/2021 |
| WO | 2022/048792 | 3/2022 |
| WO | 2022/144197 | 7/2022 |

* cited by examiner

INSECT FARMING WITH PRE-DOSED UNITS

CROSS-REFERENCE TO RELATED APPLICATION

This application claims priority under 35 U.S.C. § 119(a) to Europe Application No. 23197144.1 filed Sep. 13, 2023, the disclosure of which is expressly incorporated by reference herein in its entirety.

BACKGROUND

1. Field of the Invention

Embodiments relate to a dosing device for filling insects into at least one container for insect farming, wherein the insects are in a same specific growth stage, in particular as larvae, or in different specific growth stages, wherein the at least one container is filled with a substrate which has predetermined properties in order to promote growth of the insects in the at least one container, wherein the dosing device comprises at least one storage unit which is designed to store the insects. The present invention also relates to an arrangement and a method for filling the insects.

2. Discussion of Background Information

An insect's life cycle describes different growth stages (e.g., egg, larva, pupa and adult insect), wherein the duration of these growth stages and the growth stages varying depending on the species of insect. The term "insect" includes the insect in its various stages of growth. Depending on the type of insect, the growth phases can take a few days to a few weeks. In industrial insect farming, insects are bred primarily for food and animal feed. From the production of insect eggs to the rearing of adult insects, industrial insect farming covers the various growth stages of insects. After the insects hatch from the eggs as larvae, they are usually stored in containers or boxes filled with substrate in predetermined environmental conditions, where they grow into adult insects.

During storage in the containers, the larvae can also pupate into pupae, from which the adult insects grow. The substrate includes food for the larvae. The adult insects are "harvested", i.e., removed from the containers, and can then be further processed, e.g., into protein-rich end products such as oil or powder. Similar to other industries, production facilities in industrial insect farming are also largely automated.

Layouts of such production plants are disclosed in WO 2022/144197 A1, in US 2018/0070566 A1 or in CN 115968837 A. In various stations, the insects are first placed as larvae in containers filled with substrate, then the containers are stored and after a certain growth period they are removed again and emptied if necessary (e.g., when the insects have grown from larvae into adult insects). The insects as larvae can either be filled into the containers together with the substrate or separately. The containers can also be removed at predetermined intervals and, for example, after an inspection or after adding more substrate, stored again. In US 2016/0066552 A1, the content of the containers is monitored by means of cameras, wherein a dosing device being used to fill additional substrate into the containers. This removal and storage increases the effort required during insect farming.

For filling the insects as larvae and/or the substrate into the containers, dosing devices are usually provided, which comprise a weighing device. The weighing device is used to check, after filling, whether a predetermined quantity (dosage) of larvae and/or substrate is present in the respective container. WO 2022/144197 A1 or WO 2022/048792 A1 discloses a dosing device, wherein weighing is used to check whether there are enough larvae and/or enough substrate in the containers. In addition to the increased effort required by the weighing device, weighing also slows down production.

Basically, the quantity of insects as larvae depends on the substrate in the container. The substrate has properties such as material, amount, density, moisture, nutrient content, etc. Depending on which substrate with which properties is present in the container, a corresponding quantity of larvae must be dosed in order to obtain, for example, a predetermined density of the larvae (number of larvae per unit volume) and the substrate in the container in order to achieve the best possible yield in insect farming. Of course, this density also depends on the container volume.

The density of the larvae and the substrate in the container influences the growth of the insects. For this purpose, there is a known connection between the substrate in the container and the density of insects in the container to ensure the best possible breeding success.

SUMMARY

Embodiments improve insect breeding, in particular to increase the accuracy of the dosage of the insects in the container, for example depending on a substrate in the container, and thus to improve the growth of the insects in the container and the breeding success.

According to embodiments, when using the dosing device, a predetermined quantity of insects is packed in a package and stored in the at least one storage unit, wherein the predetermined quantity of insects is matched in a known ratio to the predetermined properties of the substrate in the at least one container, and in that the dosing device comprises a robot unit which is arranged in the area of the at least one storage unit and the at least one container and is designed to remove the package with the insects in the predetermined quantity from the at least one storage unit when using the dosing device and to move the package with the insects in the predetermined quantity to the at least one container and the robot unit is designed to fill the insects in the predetermined quantity from the package directly or indirectly into the substrate of the at least one container. This results in a more precise dosage of the insects depending on the given properties of the substrate, which consequently enables better growth of the insects in at least one container. In particular, it is now possible to easily, safely and reproducibly coordinate the substrate and its known properties with the quantity of insects to be filled into the container. Due to the resulting better growth of the insects in at least one container, failures in insect farming are reduced and breeding success is increased. The robot unit also eliminates the need to manually fill the insects into at least one container, which on the one hand reduces the amount of work required and on the other hand allows the filling process to be automated.

Advantageously, when using the dosing device, the package is filled with a substrate in addition to the predetermined quantity of insects, wherein the substrate has predetermined properties. On the one hand, this can ensure that the insects have sufficient moisture, nutrients, etc., to ensure their survival in the package for a certain period of time. On the other hand, residual materials from insect farming, such as insect excrement or previously used substrate, can be reused.

Advantageously, the predetermined quantity of insects and the substrate are evenly mixed in the package. Due to the homogeneous distribution of the substrate and the insects in the package, a homogeneous distribution can also be achieved during and after filling into the containers. This eliminates the need for homogenization of the substrate and insects in the container, which would otherwise be necessary.

In a preferred arrangement, the dosing device according to the invention is arranged in the region of a conveyor system, wherein the at least one container is arranged on the conveyor system. In insect farming, containers are preferably transported on conveyor systems due to the high logistical effort involved. This makes filling the insects into the containers on the conveyor system particularly efficient and easy to implement even with existing conveyor systems.

In a method according to embodiments for filling insects into at least one container with the dosing device, the insects are packed in a predetermined quantity in a package and the package is stored with the insects in the predetermined quantity in the at least one storage unit, wherein the predetermined quantity of insects is matched in a known ratio to the predetermined properties of the substrate in the at least one container, wherein the package containing the insects in the predetermined quantity is removed from the at least one storage unit by a robot unit and the robot unit moves the package containing the insects in the predetermined quantity to the at least one container and the robot unit directly or indirectly fills the insects in the predetermined quantity from the package into the substrate of the at least one container. Due to the predetermined quantity of insects depending on the given properties of the substrate, the accuracy of the dosage of the insects increases. Consequently, better growth of the insects in at least one container is enabled, thereby reducing failures in insect farming and increasing the yield. The robot unit can eliminate the need to manually fill the insects into at least one container, which reduces the amount of work required and makes the filling process more automated.

Advantageously, the robot unit fills the insects in the predetermined quantity from the package directly into the substrate of the at least one container by the robot unit opening the package and filling the insects in the predetermined quantity into the at least one container. This means that the package can be disposed of after the insects have been filled into at least one container, for example at the dosing device. There is no need to remove the package from the at least one container in a further step of insect farming, for example after storage of the at least one container.

Advantageously, the robot unit indirectly fills the insects in the predetermined quantity into the substrate of the at least one container by placing the package with the insects in the predetermined quantity into the at least one container. This is particularly advantageous, for example, in the case of biodegradable packages, since the package decomposes in the at least one container and no removal of the package from the at least one container is necessary. This also makes it possible to use packages that insects can eat through.

Preferably, before and/or simultaneously and/or after the insects in the predetermined quantity are filled into the at least one container, the at least one container is filled with the substrate. The amount of work is reduced, especially when filling at the same time, as there is no need to fill the insects and the substrate separately.

Advantageously, the robot unit fills at least one container with the substrate. This reduces the technical effort required for filling the insects, since the robot unit can carry out both filling the insects and filling the substrate into at least one container.

Embodiments are directed to a dosing device for depositing insects into at least one container for insect farming, the at least one container being provided with a container substrate having predetermined properties in order to promote growth of the insects in the at least one container. The dosing device includes at least one storage unit which is designed to store at least one package containing a predetermined quantity of insects; at least one package containing a predetermined quantity of insects being stored in the at least one storage unit; and a robot unit, which is arranged in a region of the at least one storage unit and the at least one container, is configured to remove the at least one package containing the predetermined quantity of insects from the at least one storage unit and to move the at least one package with the predetermined quantity of insects to the at least one container. The robot unit is further configured to directly or indirectly deposit the predetermined quantity of insects from the at least one package into the container substrate of the at least one container.

In embodiments, the insects can be in a specific growth stage and the specific growth stage may be as larvae.

In other embodiments, the insects may be in different specific growth stages.

According to embodiments, the predetermined quantity of insects can be matched in a ratio to the predetermined properties of the container substrate provided in the at least one container.

In accordance with embodiments, the at least one package may further contain a package substrate. The package substrate can have predetermined properties. Further, the predetermined quantity of insects and the package substrate may be evenly mixed in the at least one package.

Embodiments are directed to an arrangement for depositing insects in a certain growth stage into at least one container with the above-described dosing device and includes a conveyor system for moving the at least one container. The at least one container is arranged on the conveyor system, and the dosing device is arranged in a region of the conveyor system.

In other embodiments, the certain growth stage can be as larvae.

Embodiments are directed to a method for depositing insects into at least one container with the above-described dosing device. The least one container is provided with a container substrate which has predetermined properties to promote growth of the insects in the at least one container, a predetermined quantity of insects are packed in the at least one package and the at least one package is stored in the at least one storage unit. The method includes removing the at least one package with the predetermined quantity of insects from the at least one storage unit by a robot unit, and moving, via the robot unit, the at least one package with the predetermined quantity of insects to the at least one container, and depositing, directly or indirectly, the predetermined quantity of insects from the at least one package into the container substrate of the at least one container via the robot unit.

According to embodiments, the insects may be in a specific growth stage, and the specific growth stage can be as larvae.

According to other embodiments, the insects may be in different specific growth stages.

In accordance with embodiments, the predetermined quantity of insects can be matched in a ratio to the predetermined properties of the container substrate provided in the at least one container.

In other embodiments, the robot unit can deposit the predetermined quantity of insects from the at least one package directly into the container substrate of the at least one container by opening the at least one package and emptying the predetermined quantity of insects in the at least one package into the at least one container.

In accordance with other embodiments, the robot unit can indirectly deposit the predetermined quantity of insects into the container substrate of the at least one container by placing the at least one package with the predetermined quantity of insects into the at least one container.

According to other embodiments, at least one of before, simultaneously or after the predetermined quantity of insects are deposited into the at least one container, the at least one container can be provided with the container substrate.

In accordance with still yet other embodiments, the robot unit can provide the at least one container with the container substrate.

Other exemplary embodiments and advantages of the present invention may be ascertained by reviewing the present disclosure and the accompanying drawing.

BRIEF DESCRIPTION OF THE DRAWINGS

The present invention is described in greater detail below with reference to FIGS. 1 to 4, by way of example, schematic, and non-limiting advantageous embodiments of the invention. In the figures.

DETAILED DESCRIPTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figures 1, 2, 3A:
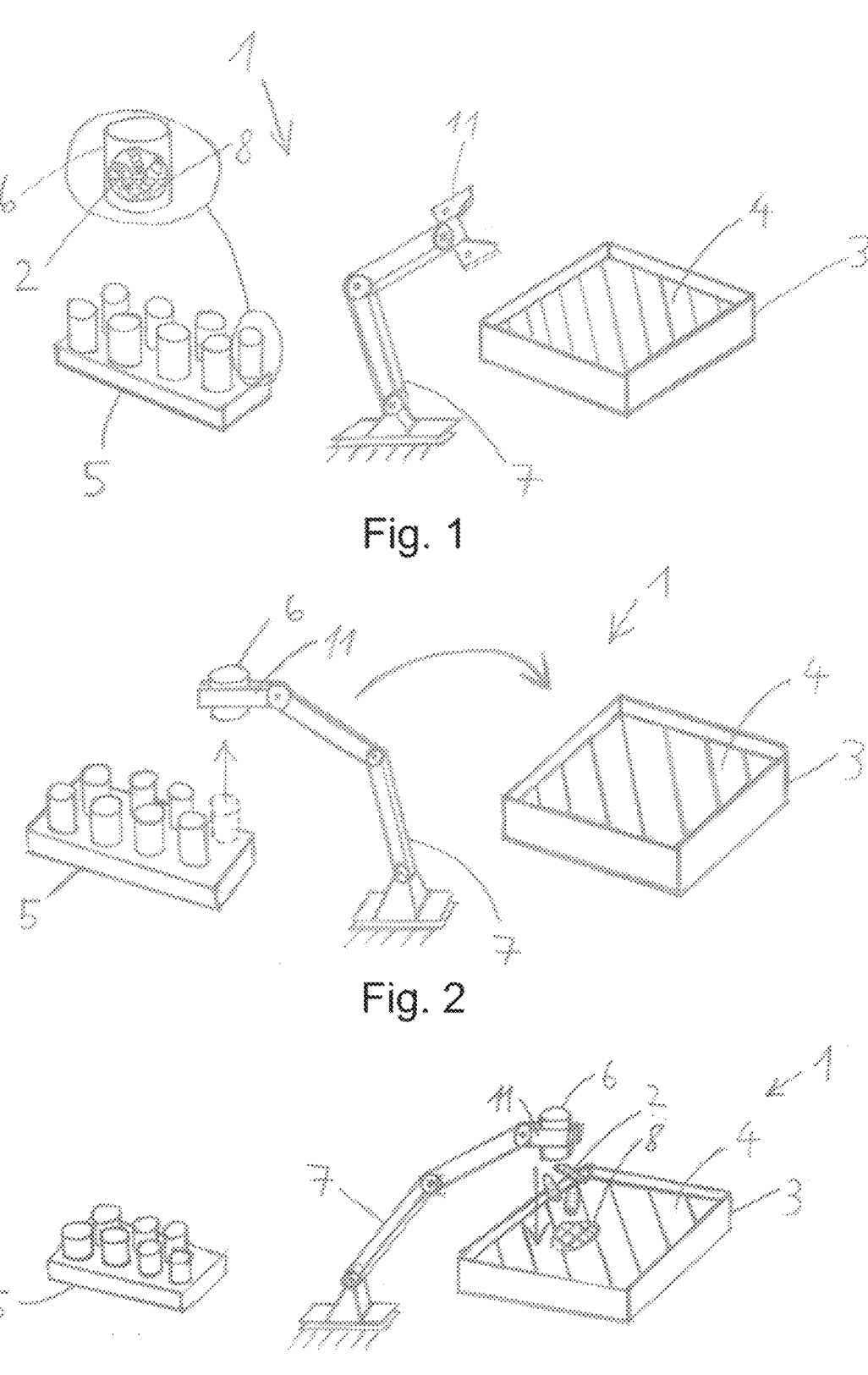
FIG. 1 shows the basic structure of the dosing device according to the invention.
FIG. 2 shows by way of example the method for filling insects with the dosing device according to the invention.
FIG. 3A shows by way of example direct filling of the insects.

FIG. 1 shows the basic structure of the dosing device 1 according to the invention for filling or depositing insects 2 into at least one container 3 for insect farming. The dosing device 1 comprises a robot unit 7 and at least one storage unit 5. The at least one storage unit 5 is arranged in the working area of the robot unit 7 and is designed to store the insects 2.

A robot unit 7 is generally a single- or multi-axis manipulator (e.g., a robot arm) with at least one gripper 11 for gripping and holding an object, in particular a package 6.

The robot unit 7 has a work area in which the gripper 11 can move, for example, to perform a "pick and place" task.

The robot unit 7 is preferably designed as an industrial robot. The robot unit 7 also comprises a robot controller by which the movement of the robot unit 7, in particular of the gripper 11, is controlled. Furthermore, the robot unit 7 can also comprise sensors which serve, for example, to control the robot unit 7.

The insects 2 to be placed in a container 3 are in a certain stage of growth. The insects 2 may all be in the same stage of growth, in particular as larvae (such as in FIG. 1) or as eggs, pupae, etc., or they may be in different specific growth stages. The insects 2 can in particular comprise those species of insects 2 which are suitable for insect farming (e.g., larvae of a black soldier fly).

In FIG. 1, a container 3 is shown, and it is to be understood, of course, that a plurality of containers 3 can be provided for containing insects 2. The at least one container 3 can be designed in different shapes and materials, such as shown in FIG. 1, as an upwardly open, rectangular crate or box, with four side walls and a base plate, each made of plastic. The container 3 can also have several separate chambers. The at least one container 3 serves, in addition to accommodating insects 2, to accommodate a substrate 4 which has predetermined properties (such as material, amount, density, moisture, nutrient content, etc.) in order to promote growth of the insects 2 in at least one container 3. Suitable substrate 4 may include vegetables, grains, fruits, starch or similar.

When using the dosing device 1, a predetermined quantity of insects 2 is packed in a package 6 and stored in at least one storage unit 5. The predetermined quantity of insects 2 is matched in a known ratio to the predetermined properties of the substrate 4 in at least one container 3. For example, depending on the customer's wishes, a density of the insects 2 (number of insects 2 per unit volume) and the amount of substrate 4 in at least one container 3 can be specified, wherein the quantity of insects 2 is accordingly matched to the specified properties of the substrate 4 (e.g., also specified by the customer).

In FIG. 1, a plurality of packages 6 in a storage unit 5 are shown by way of example, wherein one package 6 is shown enlarged merely for illustration purposes and partially broken open for a view into the package 6. The package 6 is designed, for example, with a cylindrical shape (e.g., as a cup). Of course, the shape of the package 6 is not limited this exemplary cylindrical shape and may in particular also be designed as a bag, box, etc. The package 6 can also be divided into package units, e.g., a package with a plurality of chambers in which the insects 2 are deposited or filled. The package 6 can be made of different materials, e.g., plastic, paper, cardboard, etc. The package 6 can also be made of a biodegradable material, e.g., from a biodegradable plastic, paper, cardboard, etc. Furthermore, the package 6 is preferably closed, e.g., a cup with a lid or by sealing a plastic, in order to prevent the insects 2 from escaping into the storage unit 5. The package 6 can also be open, e.g., a cup without a lid.

In addition to the insects 2, the package 6, as shown in FIG. 1, can also be filled or provided with a substrate 8, wherein the substrate 8 in the package 6 has predetermined properties. The substrate 8 in the package 6 can have the same or different properties as the substrate 4 in the container 3. The substrate 8 creates conditions for the insects 2 in the package 6 (e.g., sufficient moisture, food, nutrients, etc.) so that the insects 2 survive even when the package 6 is stored for a certain period of time, such as several days or weeks. Suitable substrates 8 include gelatin, agartine (agar-agar), cereal mixtures or similar. However, the substrate 8 in the package 6 can also comprise residual materials from insect farming, such as excrements from insects 2 or previously used substrate. The substrate 8 and the insects 2 are preferably evenly mixed by mixing (also referred to as homogenization) before being packed into the package 6. In particular, the number of insects 2 in the package 6 and the specified properties of the substrate 8, such as amount, density, moisture, nutrient content, etc., are coordinated.

In FIG. 1, a storage unit 5 is shown, and it is to be understood that a plurality of storage units 5 can also be provided. Storage unit 5 has at least one package receptacle for receiving a package 6 with insects 2. The storage unit 5 can be designed in different ways. In FIG. 1, e.g., a box shaped storage unit is shown in which the majority of packages 6 are arranged in a grid pattern. The storage unit 5 can also be designed to be stackable in order to stack a plurality of storage units 5. Predetermined environmental conditions can prevail in the storage unit 5 for storing the package 6, e.g., the storage unit 5 or the environment of the storage unit 5 can be tempered in order to keep the insects 2 in the package 6 at a certain temperature for storage.

The robot unit 7 is arranged in the region of the at least one storage unit 5 and the at least one container 3, so that the working area of the robot unit 7 at least partially encompasses the storage unit 5 and the container 3. The robot unit 7 could also be self-propelled and movable along the floor. The robot unit 7 can, for example, also be mounted on a movable platform in order to move between the storage unit 5 and the container 3.

The robot unit 7 is designed to remove the package 6 with the predetermined quantity of insects 2 from the storage unit 5 and to move the package 6 with the predetermined quantity of insects 2 to the container 3. The robot unit 7 is further designed to deposit or empty the predetermined quantity of insects 2 from the package 6 into the substrate 4 of the container 3 directly or indirectly (shown in FIGS. 3*a* and 3*b*). The robot unit 7, such as shown in FIG. 1, preferably has at least one gripper 11.

FIG. 2 shows by way of example a method for inserting or depositing the insects 2 into the container 3 with the basic structure of the dosing device 1 according to the invention. The container 3 is preferably filled or provided with the substrate 4 before the predetermined quantity of insects 2 are deposited into the container 3 in the Furthermore, the container 3 can also be filled or provided with the substrate 4 at the same time and/or after the insects 2 have been deposited or filled in the predetermined quantity. For this purpose, the dosing device 1 can comprise a filling device (not shown) which inserts and fills or provides container 3 with the substrate 4, e.g., by a trough auger conveyor or the like. Preferably, however, the substrate 4 is filled or provided into the container 3 by the robot unit 7. The robot unit 7 can also be designed to control the filling device (e.g., with the robot control) in order to fill or provide container 3 with substrate 4.

In FIG. 2 the container 3 is already filled or provided with substrate 4. The robot unit 7 then removes a package 6 with the insects 2 in the predetermined quantity from the storage unit 5, e.g., by grasping and lifting package 6 with the gripper 11. It is also possible for the robot unit 7 to simultaneously remove a plurality of packages 6 from the storage unit 5. The storage unit 5 can, for example, also comprise a conveyor system (not shown) with which the packages 6 are conveyed from the storage unit 5 to the robot unit 7, wherein the robot unit 7 removes the packages 6 from the conveyor system. The robot unit 7 then moves the package 6 with the insects 2 in the predetermined quantity to the container 3 (indicated by an arrow) so that the robot unit 7 can insert or deposit the insects 2 in the predetermined quantity from the package 6 into the substrate 4 of the container 3 directly or indirectly.

FIG. 3A by way of example shows direct inserting or depositing of the insects 2 in the predetermined quantity from the package 6 into the substrate 4 of the container 3. In this context, "directly" means that the robot unit 7 opens the package 6 (if the package 6 is closed) and deposits or empties the insects 2 in the predetermined quantity into the container 3. The package 6 is opened by the robot unit 7, for example by punching, cutting, etc., wherein the insects 2 can be emptied from the package 6 and deposited onto the substrate 4 of the container 3. In the case of an open package 6, e.g., a cup without a lid, the robot unit 7 can simply tilt or rotate the package 6 to empty the insects 2 from the package 6 so that the insects 2 reach the substrate 4 of the container 3. As shown in FIG. 3*a*, the substrate 8 located in the package 6 would also pass from the package 6 into the substrate 4 of the container 3. After the package 6 has been emptied, it can be disposed of as waste by the robot unit 7, for example.

Figure 3B:
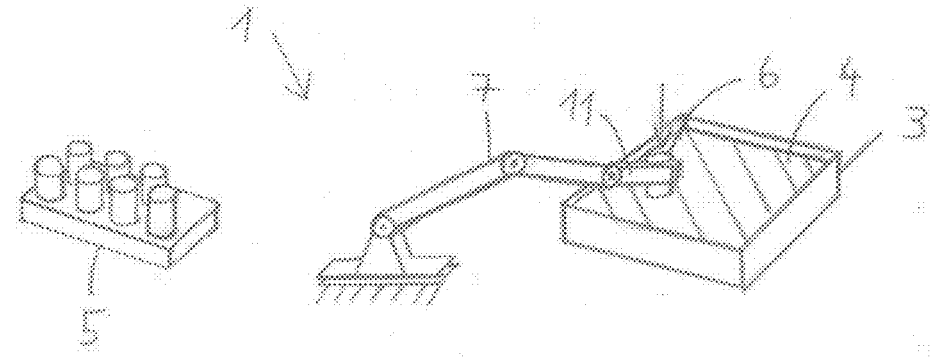
FIG. 3B shows by way of example indirect filling of the insects.

FIG. 3B by way of example shows indirect filling or depositing of the insects 2 in the predetermined quantity from the package 6 into the substrate 4 of the container 3. In this context, "indirect" means that the package 6 with the insects 2 in the predetermined quantity is placed by the robot unit 7 into the container 3. The package 6 can also be opened first by the robot unit 7, but the package 6 with the insects 2 is placed in the container 3. It is also possible that the package 6, e.g., if it is made of a biodegradable material, decomposes in the container 3 and thereby opens at least partially. It would also be possible that the package 6, e.g., if it is made of a material that is edible for the insects 2 in the package 6, is consumed by the insects 2 in the package 6, thereby at least partially opening the package 6. In this way, package 6 would not even have to be opened before being placed in container 3. Thus, the insects 2 enter the substrate 4 of the container 3. In addition, there is no need to remove the package 6 from container 3. The package 6 can also be designed to be consumed by the insects 2 in the container 3.

Figure 4:
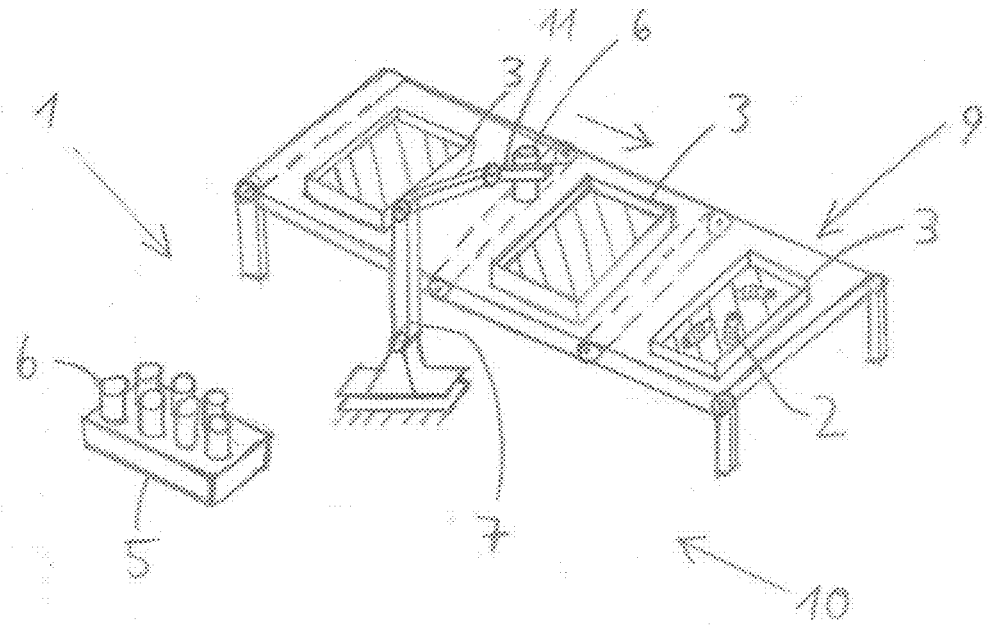
FIG. 4 shows a preferred arrangement of the dosing device according to the invention.

FIG. 4 shows a preferred arrangement 10 of the dosing device 1 according to the invention, wherein the dosing device 1 is arranged in the region of a conveyor system 9 and the at least one container 3 is arranged on the conveyor system 9 and is moved with the conveyor system 9. For example, as shown in FIG. 4, a conveyor belt can be provided on which a plurality of containers 3 filled or provided with substrate 4 are arranged. The conveyor belt is designed to move the containers 3 in a conveying direction (indicated by an arrow). The robot unit 7 fills with or deposits into the containers 3 one after the other (in the conveying direction) insects 2 from the packages 6. As shown in FIG. 4, for example, the foremost container 3 in the conveying direction is already filled or provided with insects 2 and can be further used in insect farming (e.g., for storing the container 3). The containers 3, which have been filled or provided with insects 2 are moved further by the conveyor system 9 and thereby reach another area of an insect farming facility, for example, a warehouse. The containers 3, which have been filled or provided with insects 2 are stacked on top of each other in a shelf storage area and stored for a predetermined period of time, wherein the insects 2 continue to grow in the containers 3.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A dosing device for depositing insects into at least one container for insect farming, the at least one container being provided with a container substrate having predetermined properties in order to promote growth of the insects in the at least one container, the dosing device comprising:

at least one storage unit which is designed to store at least one package containing a predetermined quantity of insects;

at least one package containing a predetermined quantity of insects being stored in the at least one storage unit, wherein the predetermined quantity of insects is matched in a known ratio to the predetermined properties of the container substrate provided in the at least one container; and a robot unit, which is arranged in a region of the at least one storage unit and the at least one container, is configured to remove the at least one package containing the predetermined quantity of insects from the at least one storage unit and to move the at least one package with the predetermined quantity of insects to the at least one container, wherein the robot unit is further configured to directly or indirectly deposit the predetermined quantity of insects from the at least one package into the container substrate of the at least one container.

2. The dosing device according to claim 1, wherein the insects are in a specific growth stage.

3. The dosing device according to claim 2, wherein the specific growth stage is as larvae.

4. The dosing device according to claim 1, wherein the insects are in different specific growth stages.

5. The dosing device according to claim 1, wherein the at least one package further contains a package substrate.

6. The dosing device according to claim 5, wherein the package substrate has predetermined properties.

7. The dosing device according to claim 5, wherein the predetermined quantity of insects and the package substrate are evenly mixed in the at least one package.

8. An arrangement for depositing insects in a certain growth stage into at least one container with the dosing device according to claim 1, comprising:

a conveyor system for moving the at least one container, wherein the at least one container is arranged on the conveyor system, and wherein the dosing device is arranged in a region of the conveyor system.

9. The arrangement according to claim 8, wherein the certain growth stage is as larvae.

10. A method for depositing insects into at least one container with the dosing device according to claim 1, the at least one container is provided with a container substrate which has predetermined properties to promote growth of the insects in the at least one container, a predetermined quantity of insects are packed in the at least one package and the at least one package is stored in the at least one storage unit, wherein the predetermined quantity of insects is matched in a known ratio to the predetermined properties of the container substrate provided in the at least one container, the method comprising:

removing the at least one package with the predetermined quantity of insects from the at least one storage unit by a robot unit, and moving, via the robot unit, the at least one package with the predetermined quantity of insects to the at least one container, and depositing, directly or indirectly, the predetermined quantity of insects from the at least one package into the container substrate of the at least one container via the robot unit.

11. The method according to claim 10, wherein the insects are in a specific growth stage.

12. The method according to claim 11, wherein the specific growth stage is as larvae.

13. The method according to claim 10, wherein the insects are in different specific growth stages.

14. The method according to claim 10, wherein the robot unit deposits the predetermined quantity of insects from the at least one package directly into the container substrate of the at least one container by opening the at least one package and emptying the predetermined quantity of insects in the at least one package into the at least one container.

15. The method according to claim 10, wherein the robot unit indirectly deposits the predetermined quantity of insects into the container substrate of the at least one container by placing the at least one package with the predetermined quantity of insects into the at least one container.

16. The method according to claim 10, wherein at least one of before, simultaneously or after the predetermined quantity of insects are deposited into the at least one container, the at least one container is provided with the container substrate.

17. The method according to claim 10, wherein the robot unit provides the at least one container with the container substrate.

18. The arrangement according to claim 7, wherein the conveyor system is a conveyor belt on which a plurality of containers is arranged.

19. The dosing device according to claim 1, wherein the robot unit is an industrial robot, in particular a robot arm.

20. The method according to claim 10, wherein as the robot unit an industrial robot, in particular a robot arm is used.

* * * * *